(12) United States Patent
Orth et al.

(10) Patent No.: US 10,292,844 B2
(45) Date of Patent: May 21, 2019

(54) METHOD FOR COMPRESSING A STENTED PROSTHESIS

(71) Applicant: Medtronic Vascular, Inc., Santa Rosa, CA (US)

(72) Inventors: Geoffrey Orth, Sebastopol, CA (US); Kenny Bruner, Santa Rosa, CA (US); Don Tran, Novato, CA (US); Jill Mendelson, San Francsico, CA (US); James R. Keogh, Maplewood, MN (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 327 days.

(21) Appl. No.: 15/156,538

(22) Filed: May 17, 2016

(65) Prior Publication Data
US 2017/0333228 A1 Nov. 23, 2017

(51) Int. Cl.
*B21D 39/04* (2006.01)
*A61F 2/844* (2013.01)
(Continued)

(52) U.S. Cl.
CPC ............ *A61F 2/844* (2013.01); *A61F 2/2415* (2013.01); *A61F 2/95* (2013.01); *B21D 39/04* (2013.01);
(Continued)

(58) Field of Classification Search
CPC .... A61F 2/2415; A61F 2/2433; A61F 2/2436; A61F 2/1962; A61F 2/844; B21D 39/04; B21D 39/046; Y10T 29/49913; Y10T 29/49925; Y10T 29/53996; Y10T 29/53987
See application file for complete search history.

(56) References Cited

U.S. PATENT DOCUMENTS 8,468,667 B2   6/2013   Straubinger et al.
8,585,019 B2   11/2013   Melsheimer et al.
(Continued)

FOREIGN PATENT DOCUMENTS

DE   20306823 U1   11/2003

OTHER PUBLICATIONS

PCT/US2017/027712, The International Search Report and the Written Opinion of the International Searching Authority, dated Sep. 5, 2017.

*Primary Examiner* — Jermie E Cozart

(57) ABSTRACT

A tool for compressing a stented prosthesis. The tool includes first and second sets of rollers. The first set includes a plurality of rollers arranged to define a first working region having a first working diameter. The second set includes a plurality of rollers arranged to define a second working region having a second working diameter. The sets of rollers are arranged such that the working regions are axially aligned. The first working diameter is greater than the second working diameter. A stented prosthesis traversing the first working region and then the second working region is forced to a compressed state. In some embodiments, the tool includes one or more intermediate sets of rollers between the first and second sets of rollers, with each of the intermediate sets of rollers defining a working region having a working diameter. The respective working diameters progressively decrease in a downstream direction.

8 Claims, 10 Drawing Sheets

(51) Int. Cl.
*A61F 2/24* (2006.01)
*A61F 2/95* (2013.01)
*B21D 39/06* (2006.01)
*A61F 2/962* (2013.01)

(52) U.S. Cl.
CPC .......... *A61F 2/2433* (2013.01); *A61F 2/2436* (2013.01); *A61F 2/962* (2013.01); *A61F 2002/9522* (2013.01); *B21D 39/06* (2013.01); *Y10T 29/49913* (2015.01); *Y10T 29/49925* (2015.01); *Y10T 29/53987* (2015.01); *Y10T 29/53996* (2015.01)

(56) References Cited

U.S. PATENT DOCUMENTS

| | | |
|---|---|---|
| 8,608,795 B2 | 12/2013 | Melsheimer et al. |
| 8,747,458 B2 | 6/2014 | Tuval et al. |
| 2006/0100689 A1 | 5/2006 | Pryor |
| 2010/0049313 A1* | 2/2010 | Alon ................ A61F 2/2418 623/2.11 |
| 2010/0185207 A1 | 7/2010 | Voelkl |
| 2010/0185277 A1* | 7/2010 | Braido ............. A61F 2/2412 623/2.18 |
| 2011/0056064 A1 | 3/2011 | Malewicz et al. |
| 2013/0283596 A1 | 10/2013 | Golan et al. |
| 2014/0230515 A1 | 8/2014 | Tuval et al. |

* cited by examiner

METHOD FOR COMPRESSING A STENTED PROSTHESIS

BACKGROUND

The present disclosure relates to tools for compressing or crimping a stented prosthesis. More particularly, it relates to tools and methods for progressively reducing the outer profile of a stented prosthesis, for example a stented prosthetic heart valve.

Stents are cylindrical-shaped devices that are radially expandable to hold open a segment of a vessel or other anatomical lumen after implantation into the lumen. Various types of stents are in use, including expandable and self-expanding stents. Expandable stents generally are conveyed to the area to be treated on balloon catheters or other expandable devices. For a self-expanding stent, commonly a sheath is retracted, allowing expansion of the stent.

Bioprosthetic stent devices are employed in a variety of surgical treatments. For example, a stent can be designed for use in counteracting restenosis, or the repeated narrowing of a blood vessel. In other applications, a stent can be utilized as part of a stented prosthetic heart valve. A stented heart valve prosthesis employed with catheter-based, or transcatheter, procedures generally includes an expandable multi-level frame or stent that supports a valve structure having a plurality of leaflets. The frame can be contracted during percutaneous transluminal delivery, and expanded upon deployment at or within the native valve. One type of valve stent can be initially provided in an expanded or uncrimped condition, then crimped or compressed about a balloon portion of an inner catheter or inner shaft. The balloon is subsequently inflated to expand and deploy the prosthetic heart valve. With other stented prosthetic heart valve designs, the stent frame is formed to be self-expanding. With these systems, the valved stent is crimped down to a desired size over an inner shaft and held in that compressed state within an outer sheath for transluminal delivery. Retracting the sheath from this valved stent allows the stent to self-expand to a larger diameter, fixating at the native valve site. In more general terms, then, once the prosthetic valve is positioned at the treatment site, for instance within an incompetent native valve, the stent frame structure may be expanded to hold the prosthetic valve firmly in place. One example of a stented prosthetic valve is disclosed in U.S. Pat. No. 5,957,949 to Leonhardt et al., which is incorporated by reference herein in its entirety.

Regardless of design (e.g., expandable or self-expanding) and end-use application, a stented prosthesis is normally collapsed or crimped to a smaller profile by a specialized tool for placement on or in the corresponding delivery device. For example, tools incorporating a conical- or funnel-shaped loading device are known. With these tools, the stented prosthesis is pulled or otherwise directed through the funnel-shaped device, forcing the stent to collapse to a reduced diameter profile. Alternatively, crimping tools are known that include a plurality of segments or jaws arranged to define a chamber (e.g., an iris type camber, a star-type chamber, or other geometric configuration) and translatable relative to one other in selectively reducing a size of the chamber (and thus a profile a stented prosthesis located within the chamber).

With many stent-based surgical procedures, it is desirable to affect as small a profile as possible into the stented prosthesis for delivery to the target site so as to minimize invasiveness of the procedure and enhance patient safety. While generally viable, existing compression tools are unable to effectuate desired profile reductions in some stented prosthetic devices, such as self-expanding stented prosthetic heart valves. Further, existing compression tools oftentimes generated bulges, or bumps or other non-uniformities in the collapsed stented prosthesis; these non-uniformities are undesirable as they can "catch" on human anatomy while being tracked to the target site.

SUMMARY

The inventors of the present disclosure recognized that a need exists for tools for compressing a stented prosthesis that overcomes one or more of the above-mentioned problems.

Some aspects of the present disclosure relate to a tool for compressing a stented prosthesis. The tool includes first and second sets of rollers. The first set of rollers includes a plurality of rollers arranged to define a first working region having a first working diameter. The second set of rollers includes a plurality of rollers arranged to define a second working region having a second working diameter. The sets of rollers are arranged such that the working regions are axially aligned. Further, the first working diameter is greater than the second working diameter. With this construction, a stented prosthesis traversing the first working region and then the second working region can be compressed from a first state to a second state. In some embodiments, the tool defines an entrance side opposite an exit side, with the first set of rollers located immediately adjacent the entrance side and the second set of rollers located immediately adjacent the exit side. In related embodiments, the tool further includes one or more intermediate sets of rollers between the first and second sets of rollers, with each of the intermediate sets of rollers defining a working region having a working diameter. The respective working diameters progressively decrease from the entrance side to the exit side.

Other aspects of the present disclosure relate to methods for compressing a stented prosthesis. A stented prosthesis in a first state is received and then inserted into a tool as described above. As the stented prosthesis progresses through the sets of rollers, the stented prosthesis is forced to compress to a second state. In some embodiments, the stented prosthesis is a stented prosthetic heart valve, and the method of compressing includes loading the compressed stented prosthetic heart valve into or on to a delivery device.

DETAILED DESCRIPTION

Figure 1:
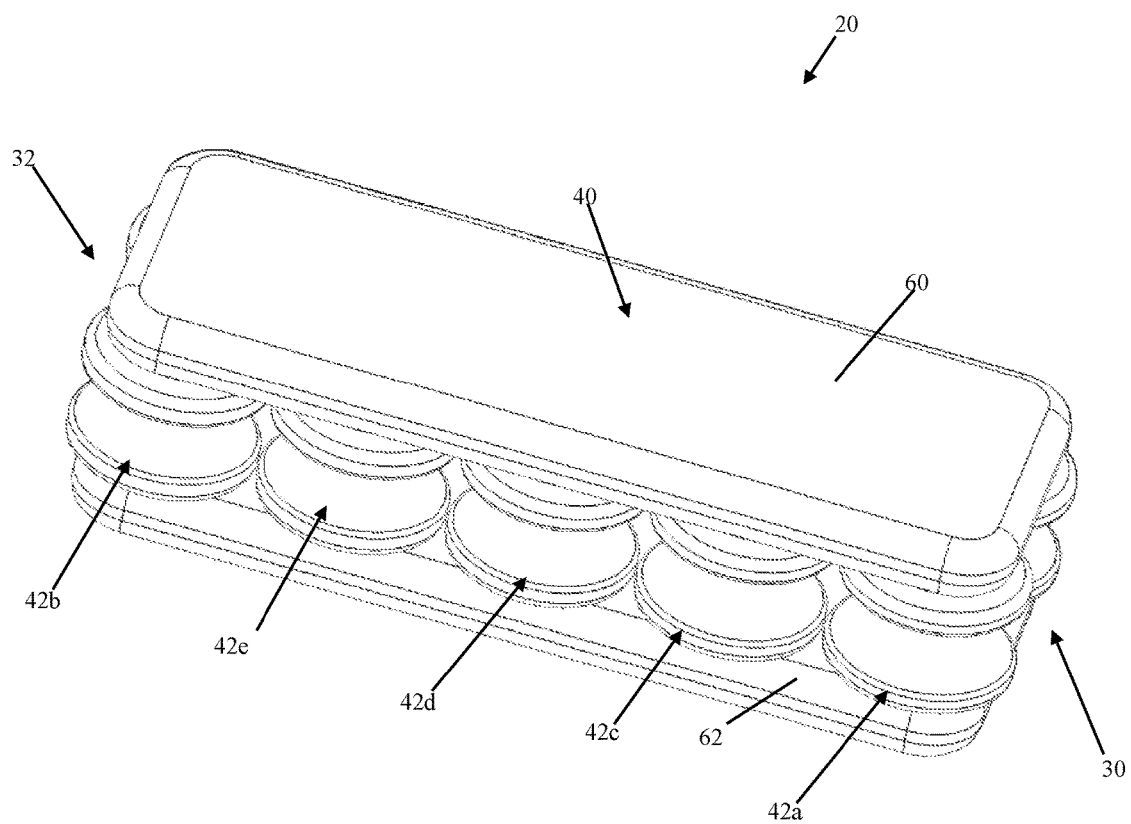
FIG. 1 is a perspective view of a compressing tool in accordance with principles of the present disclosure.

One embodiment of a stented prosthesis compressing tool 20 is provided in FIG. 1. As a point of reference, the tools of the presented disclosure can be employed in loading a stented prosthesis on to a delivery device; thus, the tools of the present disclosure (including the compressing tool 20 of FIG. 1) can alternatively be referred to as a "stented prosthesis loading tool". The tool 20 defines an entrance side 30 (referenced generally) opposite an exit side 32 (referenced generally), and includes a housing 40 maintaining at least two sets of rollers, such as a first set of rollers 42a and a second set of rollers 42b. The first set of rollers 42a is located immediately adjacent the entrance side 30 and thus can alternatively be referenced as the entrance side set of rollers 42a; conversely, the second set of rollers 42b is located immediately adjacent the exit side 32 and thus can alternatively be referenced as the exit side set of rollers 42b. With the non-limiting example of FIG. 1, third-fifth sets of rollers 42c-42e can also be provided intermediate the entrance side set of rollers 42a and the exit side set of rollers 42b. In other embodiments, more or less than five sets of rollers are included. Regardless of number, the sets of rollers 42a-42e are arranged to define aligned working regions that progressively decrease in diameter from the entrance side 30 to the exit side 32 as described in greater detail below. With this construction, a stented prosthesis (not shown) in a first state can be inserted into the tool 20 at the entrance side 30, progressed through the sets of rollers 42a-42e, and compressed or forced to a second state at the exit side 32, with a diameter or profile of the stented prosthesis in the second state being less than that of the first state.

Figure 2A:
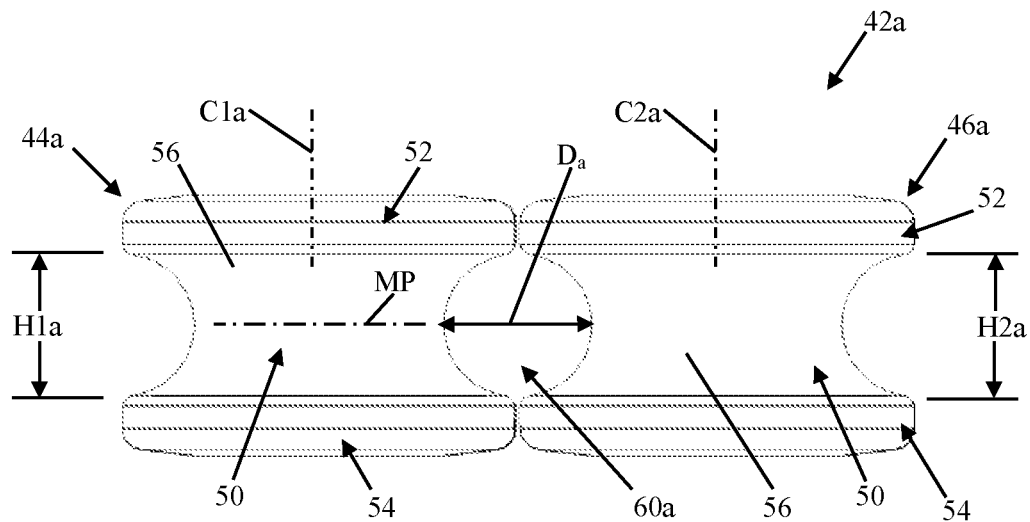
FIG. 2A is an end view of a first set of rollers useful with the tool of FIG. 1.

The first set of rollers 42a is shown in isolation in FIG. 2A, and includes first and second rollers 44a, 46a. As a point of reference, although the housing 40 (FIG. 1) is not shown in FIG. 2A, a relationship between the rollers 44a, 46a reflected by the view of FIG. 2A corresponds with that effectuated upon final assembly with the housing 40; in other words, although the rollers 44a, 46a are illustrated apart from a remainder of the tool 20 (FIG. 1), the arrangement and relationship (described below) of the rollers 44a, 46a relative to one another in the view of FIG. 2A is established by or within the housing 40.

In some embodiments, the rollers 44a, 46a can be identical such that the following description of the first roller 44a applies equally to the second roller 46a. The roller 44a is configured to define a central axis C1a, and includes or defines an engagement section 50 and opposing, first and second flanges 52, 54. The engagement section 50 can be symmetrical about the central axis C1a, and generates an outer surface 56 that forms a concave shape in some embodiments as shown. The outer surface 56 can be highly smooth. Further, the concave shape can be uniform between the opposing flanges 52, 54. For example, a shape of the outer surface 56 can be bisected by a mid-line plane MP perpendicular to the central axis C1a; the outer surface 56 defines a diameter that progressively increases from the mid-line plane MP to the opposing flanges 52, 54. A diameter of each of the opposing flanges 52, 54 is greater than that of the outer surface 56 of the engagement section 50 at least at the mid-line plane MP. Geometry features of the roller 44a can alternatively be identified with respect to a height H1a of the engagement section 50 between the opposing flanges 52, 54 as described below.

The roller 44a can be an integral, homogenous body, or can be formed by two or more separately-formed parts. Various materials (and combinations of materials) can be employed so long as the roller 44a (at least at the outer surface 56) is sufficiently stiff or hardened so as to not overtly deform in the presence of expected forces during use (e.g., the outer surface 56 will not overtly deflect, collapse or deform when acting to force a stented prosthetic heart valve to a reduced profile). Though not visible in the view, a central bore can be formed through the engagement section 50 and one or both of the flanges 52, 54 along the central axis C1a for receiving a pin, spindle, axle or similar body and about which the roller 44a can rotate.

Upon final assembly of the first set of rollers 42a (reflected by FIG. 2A), the first and second rollers 44a, 46a are transversely aligned in close proximity to one another. For example the first flange 52 of the first roller 44a is transversely aligned with the first flange 52 of the second roller 46a, and the second flanges 54 are also transversely aligned. The corresponding engagement sections 50 combine to define a working region 60a. Due to the optionally symmetric, concave shape of the opposing, aligned outer surfaces 56, at least in the plane where the engagement sections 50 are most closely adjacent to one another (i.e., the plane reflected by FIG. 2A), a shape of the working region 60a is a circle, circular or circle like, and defines a working diameter $D_a$. It will be understood that due to slight variations along the outer surfaces 56 and/or a discontinuity between the outer surface 56 of the first roller 44a and the outer surface 56 of the second roller 46a at a location of the aligned flanges 52, 54, a diameter (or other major dimension) of the working region 60a as collectively defined by the rollers 44a, 46a may vary; however, at least a majority of the working region 60a exhibits the working diameter $D_a$. Due to the uniform, concave shape of the outer surfaces, the working diameter $D_a$ can be identical to the height H1a, H2a of the engagement section 50 of the rollers 44a, 46a. In other embodiments, the working region 60a can be collectively defined by three or more rollers.

Figure 2B:
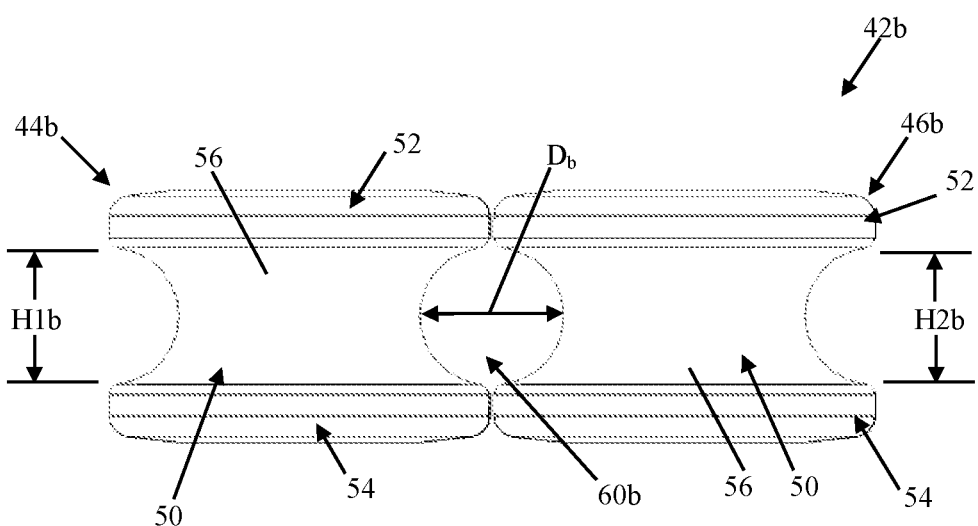
FIG. 2B is an end view of a second set of rollers useful with the tool of FIG. 1.

Returning to FIG. 1, the second-fifth sets of rollers 42b-42e can be highly akin to the first set of rollers 42a as described above, each including two (or more) rollers that can be substantially similar to the first and second rollers 44a, 46a and that collectively defining a working region (hidden in FIG. 1, but akin to the working region 60a of FIG. 2A). However, a working diameter of each successive set of rollers progressively decreases from the entrance side 30 to the exit side 32. For example, FIG. 2B is a side view of the second set of rollers 42b that includes first and second rollers 44b, 46b. Once again, the view of FIG. 2B reflects an arrangement of the rollers 44b, 46b relative to one another upon final assembly within the housing 40 (FIG. 1). The rollers 44b, 46b can be identical, and can be substantially the same as the rollers 44a, 46a (FIG. 2A) of the first set of rollers 42a (FIG. 2A) as described above. The rollers 44b, 46b each include an engagement section 50 and opposing flanges 52, 54, with an outer surface 56 of the engagement section 50 having a uniform, concave shape in extension between the corresponding flanges 52, 54. Further, the rollers 44b, 46b are arranged relative to one another such that the outer surfaces 56 collectively define a working region 60b that is circular or circle-like and has a working diameter $D_b$. Beyond these general similarities with the roller 44a, 46a of the first set of rollers 42a, the rollers 44b, 46b of the second set of rollers 42b are configured to establish or generate the working diameter $D_b$ as being less than the working diameter $D_a$ (FIG. 2A) of the first set of rollers 42b. Differences between the first and second sets of rollers 42a, 42b can optionally be described as a height H1b, H2b of the rollers 44b, 446b of the second set of rollers 42b being less than the height H1a, H1b (FIG. 2A) of the rollers 44a, 46a of the first set of rollers 42a.

Figure 3A:
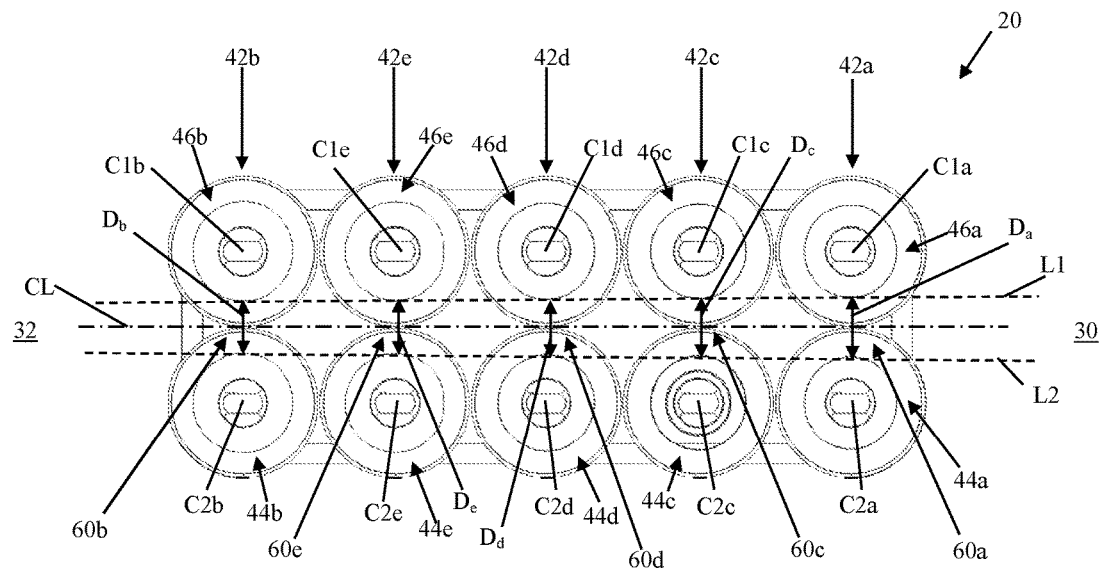
FIG. 3A is a longitudinal cross-sectional view of the tool of FIG. 1.

The longitudinal cross-sectional view of FIG. 3A reflects that upon final assembly of the tool 20, each of the sets of rollers 42a-42e defines a corresponding working region 60a-60e, and that the working regions 60a-60e are longitudinally aligned. For example, the central axis C1a-C1e of the first roller 44a-44e of each of the sets of rollers 42a-42e can be longitudinally aligned, as can the central axis C2a-C2e of the second rollers 46a-46b. Regardless, the working regions 60a-60e collectively define a common centerline CL along which a stented prosthesis (not shown) is directed during use, progressing from the entrance side 30 to the exit side 32. The working diameter $D_a$-$D_e$ of the working regions 60a-60e progressively decreases from the entrance side 30 to the exit side 32 (e.g., the third set of rollers 42c is immediately adjacent the first set of rollers 42a in the downstream direction (i.e., direction from the entrance side 30 to the exit side 32), and the working diameter $D_e$ of the third set of rollers 42c is less than the working diameter $D_a$ of the first set of rollers 42a; the fourth set of rollers 42d is immediately adjacent the second set of rollers 42c in the downstream direction, and the working diameter $D_d$ of the fourth set of rollers 42d is less than the working diameter $D_e$ of the third set of rollers 42c; etc.). In some embodiments, the sets of rollers 42a-42e are configured such that the working diameters $D_a$-$D_e$ progressively decrease in a non-linear fashion, accounting for the likelihood that as a stented prosthesis is progressively collapsed through the tool 20 from the entrance side 30 toward the exit side 32, the force required to effectuate further compression increases. To address this possible operational requirement, the sets of rollers 42a-42e can exhibit a smaller change or decrease in working diameter approaching the exit side 32 (e.g., the difference between the first (or entrance side) and third working diameters $D_a$, $D_c$ can be greater than the difference between the fifth and second (or exit side) working diameters $D_e$, $D_b$). In other embodiments, the working diameters can progressively decrease in the downstream direction in a uniform or linear fashion. Regardless, the successively decreasing size of the working regions 60a-60e from the entrance side 30 to the exit side 32 generates theoretical lines of compression L1, L2 that taper toward the center line CL in extension from the entrance side 30 to the exit side 32.

Figure 3B:
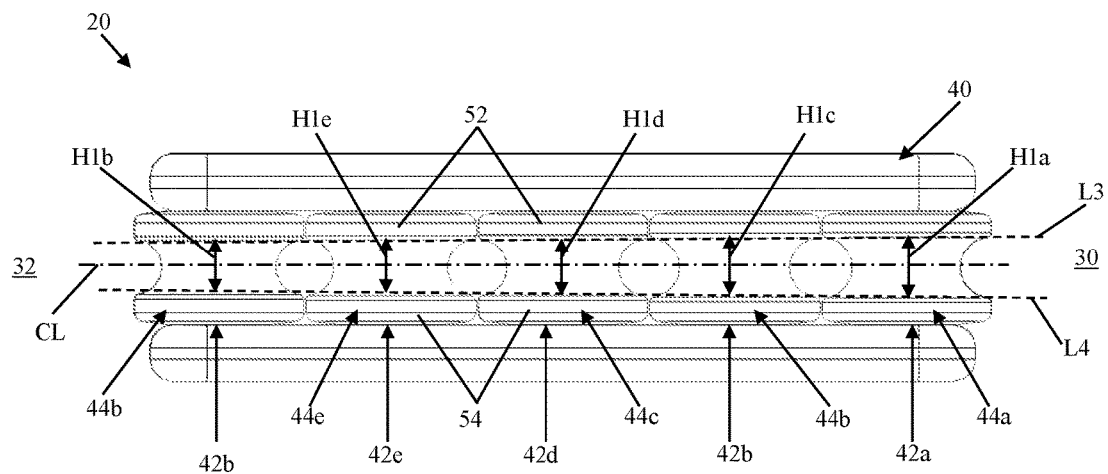
FIG. 3B is a side view of the tool of FIG. 1.

The decreasing or tapering nature of the working regions 60a-60e can alternatively be described, in some embodiments, relative to the engagement section height established by each of the rollers. For example, the view FIG. 3B illustrates the first roller 44a-44e of the first-fifth sets of rollers 42a-42e. The engagement section height H1a-H1e of each of the first rollers 44a-44e is also identified. As shown, the heights H1a-H1e progressively decrease from the entrance side 30 to the exit side 32, generating theoretical lines of compression L3, L4 that taper toward the centerline CL in a direction of the exit side 32.

With reference between FIGS. 3A and 3B, geometries of the working regions 60a-60e (e.g., the working diameters $D_a$-$D_e$) can be selected in accordance with expected attributes of the stented prosthesis (not shown) to be processed by the tool 20. For example, the working diameter $D_a$ of the first set of rollers 42a (i.e., at the entrance side 30) can be selected to generally approximate an expected, normal profile or diameter of a stented prosthesis to be processed, whereas the working diameter $D_b$ of the second set of rollers 42b (i.e., at the exit side 32) can be selected to approximate a desired, final collapsed profile or diameter of the stented prosthesis to be processed. To the extent one or more additional sets of rollers are provided between the first and second sets of rollers 42a, 42b, the working diameters of these intermediate sets of rollers can be selected to progressively decrease in the downstream direction from the working diameter $D_a$ of the first set of rollers 42a to the working diameter $D_b$ of the second set of rollers 42b. As mentioned above, while the tool 20 is shown as having three sets of rollers (i.e., the third-fifth sets of rollers 42c-42e) intermediate the first and second sets of rollers 42a, 42b, any other number, either greater or lesser, is also acceptable, and may or may not incorporate uniformly decreasing working diameters. In some non-limiting embodiments, the tool 20 is configured for compressing or collapsing a stented prosthetic heart valve, and the first (or entrance side) working diameter $D_a$ is in the range of 0.270-0.290 inch (6.858-7.366 mm), the second (or exit side) working diameter $D_b$ is in the range of 0.240-0.260 inch (6.096-6.604 mm), and the intermediate working diameters progressively decrease in diameter from the first working diameter $D_a$ in increments of 0.010 inch (0.254 mm) or 0.005 inch (0.127 mm) increments; for example, the first (entrance) working diameter $D_a$ can optionally be 0.285 inch (7.230 mm) or 0.275 inch (6.985 mm) and the second (exit) working diameter $D_b$ can optionally be 0.250 inch (6.350 mm) or 0.245 inch (6.223 mm).

FIGS. 3A and 3B further reflect that in some embodiments, the rollers of each set of rollers 42a-42e are positioned in highly close proximity to one another. For example, the first roller 44a of the first (or entrance side) set of rollers 42a is immediately adjacent the first roller 44c of the third set of rollers 42c; minimal, if any, spacing exists between the corresponding first flanges 52 (and between the corresponding second flanges 54). Stated otherwise, in some embodiments in which each set of rollers 42a-42e includes two rollers, the central axes C1a-C1e, C2a-C2e can all be substantially parallel with one another (i.e., within 5% of a truly parallel relationship) and the linear distance between the central axes C1a-C1e, C2a-Ce of an immediately adjacent ones of the rollers 44a-44e or 46a-46e closely approximates (i.e., within 5%) the diameter of the flanges 52, 54 (e.g., the linear distance between the central axis C1c of the first roller 44c of the third set of rollers 42c and the central axis C1d of the first roller 44d of the fourth set of rollers 44d closely approximates the diameter of the flanges 52, 54). With this optional construction, a stented prosthesis will be in nearly continuous contact with (and acted upon) rollers as the stented prosthesis is progressed from the entrance side 30 to the exit side 32, promoting a uniform or consistent profile in the collapsed state of the stented prosthesis as effectuated by the tool 20.

With additional reference to FIG. 1, the housing 40 can assume various forms conducive to rotatably maintain all of the rollers of the sets of rollers 42a-42e. In some non-limiting embodiments, the housing 40 can include opposing, first and second plates 60, 62 disposed at opposite ends of the sets of rollers 42a-42e as shown. The tool 20 can be constructed such that the housing 40 can be partially disassembled by as user, such as by providing a releasable coupling between the first plate 60 (and/or the second plate 62) relative to the sets of rollers 42a-42e. With these optional constructions, a user can access and release a stented prosthesis (not shown) and/or device carrying the stented prosthesis from an interior of the tool 20 by simply removing the first plate 60 (or the second plate 62). In related embodiments, one or more of the rollers of the sets of rollers 42a-42e can be spring loaded relative to the housing 40, allowing a user to selectively separate or displace one or more of the rollers from the assembled arrangement of FIGS. 1, 3A, and 3B following opening of the housing 40 so as to more easily access and release a stented prosthesis (or device carrying the stented prosthesis) from between the rollers. In yet other embodiments, the optional spring-loaded roller construction can be configured to permit a user to selectively hold or release one or more of the rollers from the normal or in-use arrangement of FIGS. 1, 3A, and 3B; with these optional embodiments, a user can selectively release one or more of the rollers to permit a larger component (e.g., a component such as a nose cone of a device carrying a stented prosthesis to be compressed) to pass through the tool 20.

Figure 4A:
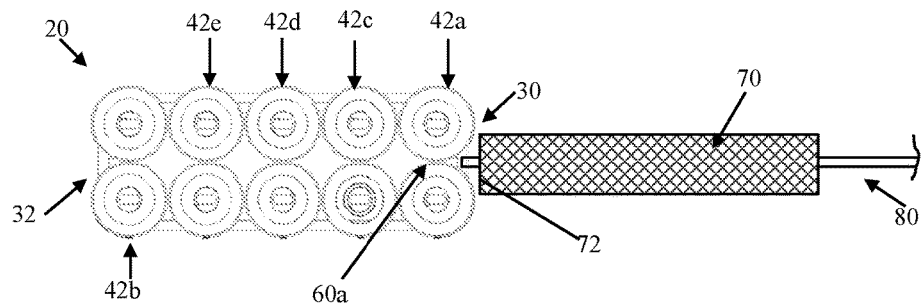
FIGS. 4A-4C are simplified top views illustrating use of the tool of FIG. 1 in compressing a stented prosthesis.
Figure 4B:
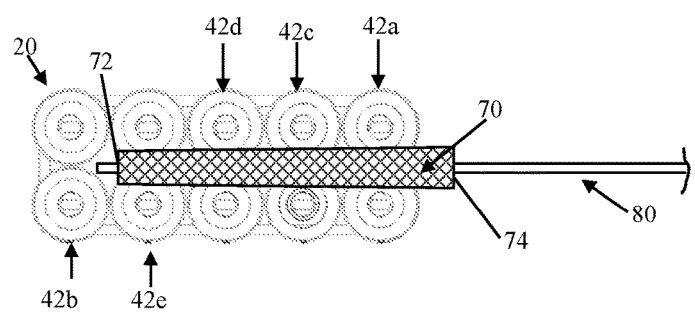
Figure 4C:
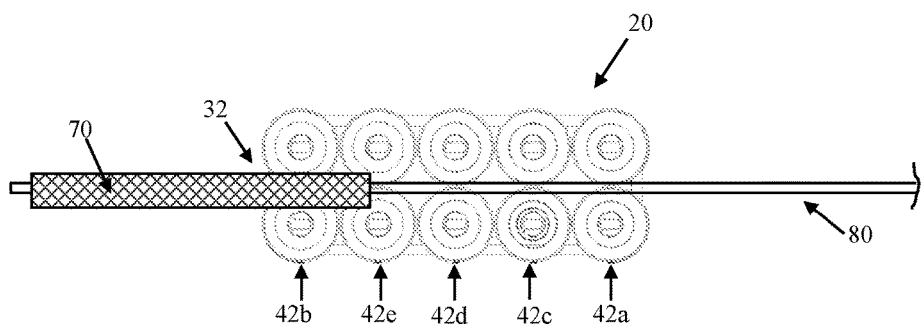

Use of the tool 20 in compressing or crimping a stented prosthesis 70 is generally shown in FIGS. 4A-4C. Initially, and with specific reference to FIG. 4A, the stented prosthesis 70 is in first or normal state and is presented to the entrance side 30 of the tool 20 (i.e., a distal end 72 of the stented prosthesis 70 is aligned with the working region 60a of the first (or entrance side) set of rollers 42a. The stented prosthesis 70 can be carried by a device 80 (shown schematically in FIGS. 4A-4C as including or being akin to a shaft). The device 80 can optionally be, or be part of, a delivery device configured for delivering the stented prosthesis 70 to a target site following compression with the tool 20. Regardless, a profile or outer diameter of the prosthesis 70 in the normal state approximates (e.g., is larger or slightly larger than) the working diameter $D_a$ (FIG. 3A) of the first (or entrance side) set of rollers 42a. The stented prosthesis 70 is then caused to progressively move through the tool 20 in the downstream direction from the entrance side 30 toward the exit side 32. In this regard, the device 80 can be manipulated to direct or force the stented prosthesis 70 longitudinally through the tool 20 (with the rollers of the sets of rollers 42a-42e freely rotating in response to contact with the longitudinally-moving stented prosthesis 70) and/or the rollers of the sets of rollers 42a-42e can be rotatably driven (manually or motorized) to grasp and "pull" the stented prosthesis 70 through the tool 20.

As the stented prosthesis 70 is directed through the tool 20, the stented prosthesis 70 interfaces with and is acted upon the rollers of each of the sets of rollers 42a-42e. For example, in the intermediate state of FIG. 4B, the stented prosthesis 70 has progressed to a location at which the distal end 72 has reached the fifth set of rollers 42e. Due to this interface, segments of the stented prosthesis 70 are progressively compressed or forced to collapse. In other words, as a particular transverse segment of the stented prosthesis progresses from one set of rollers 42a-42e to the next, immediately-downstream set of rollers 42b-42e, that particular transverse segment is progressively compressed or collapsed to a smaller profile or diameter. Consistent with this explanation, FIG. 4B schematically reflects that at this intermediate stage of operation, the distal end 72 has been compressed to smaller profile or diameter as compared to the profile or diameter at the opposing, proximal end 74.

FIG. 4C reflects an even later stage of the compression process. The stented prosthesis 70 has further progressed through the tool 20, with the sets of rollers 42a-42e having compressed an entirety of the stented prosthesis 70 to a second state at the exit end 32. A diameter or profile of the stented prosthesis 70 in the second state is less than that of the first state (as in FIG. 4A).

Figure 5:
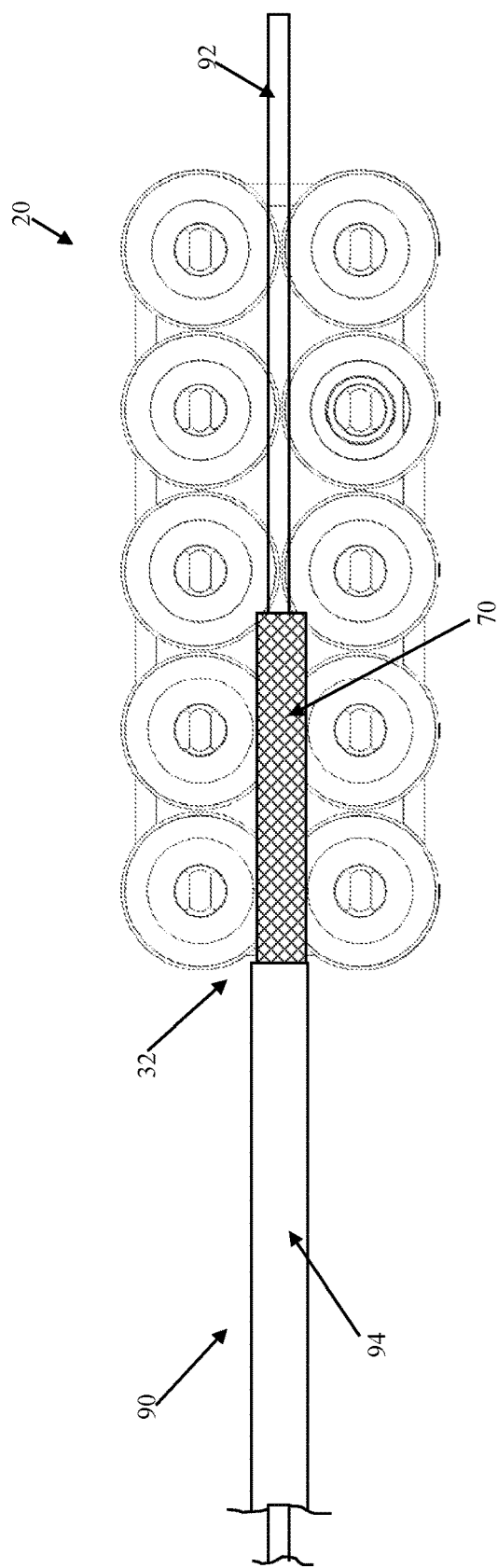
FIG. 5 is a simplified top view illustrating use of the tool of FIG. 1 in loading a stented prosthesis to a delivery device.

In some embodiments, the tool 20 can used to, and/or incorporate additional components that facilitate the performance of, loading the stented prosthesis into or onto a delivery device. For example, FIG. 5 illustrates operation of the tool 20 in compressing or collapsing the stented prosthesis 70 to a reduced profile or outer diameter at the exit side 32. The stented prosthesis 70 is carried by a device 90 that includes an inner shaft 92 and an outer capsule 94. The tool 20 and device 90 are configured such that as the stented prosthesis exits the exit side 32, it immediately enters the capsule 94 (e.g., the inner shaft 92 can slide relative to the capsule 94; the stented prosthesis 70 moves with movement of the inner shaft 92 and is brought within the capsule 94). With this but one acceptable arrangement, the stented prosthesis 70 is compressed by the tool 20 and then held or maintained in this compressed state by the capsule 94. Other, similar methods and tool components are also envisioned.

Figure 6:
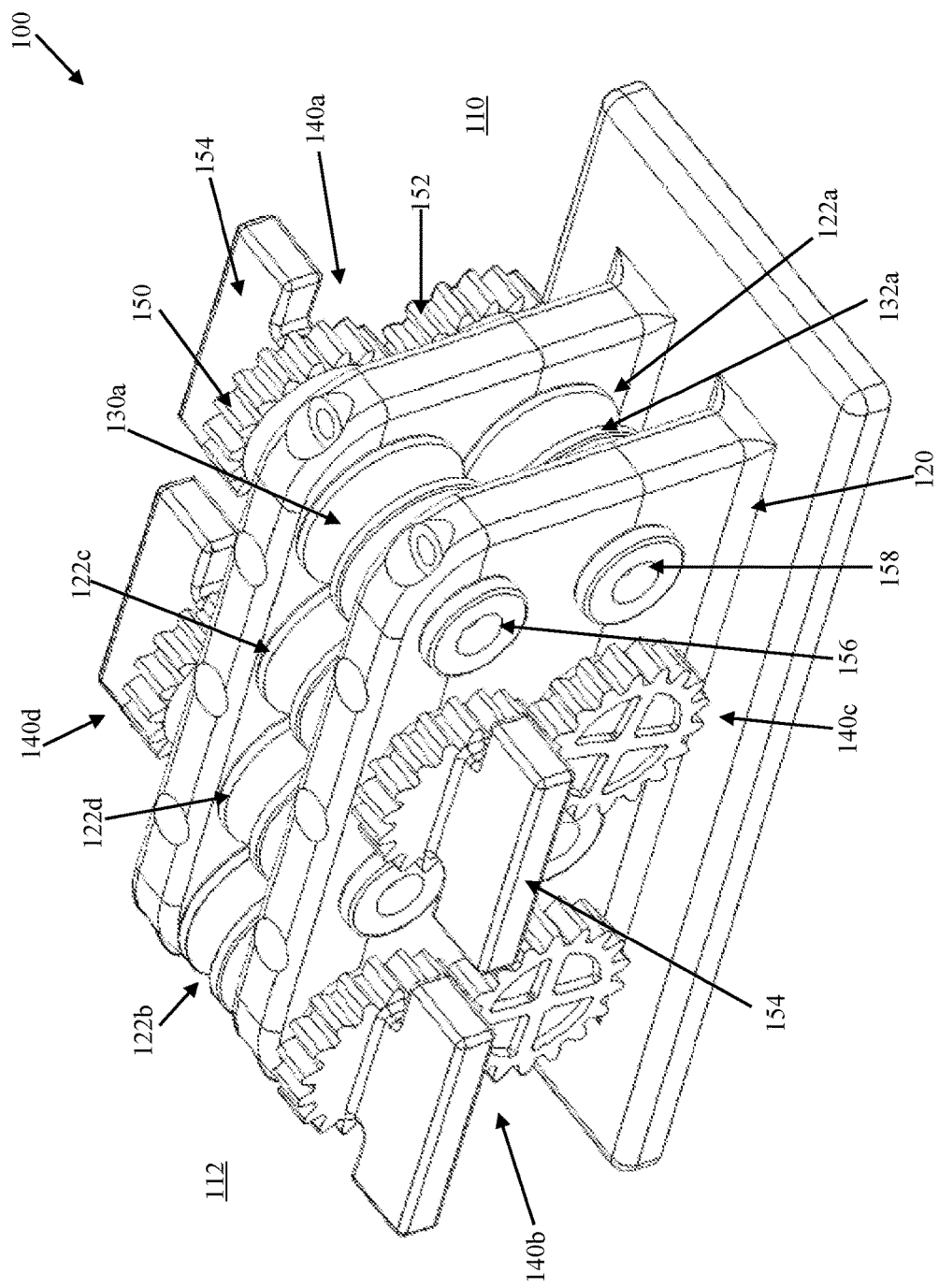
FIG. 6 is a perspective view of another tool in accordance with principles of the present disclosure.

As stated above, in some embodiments the tools of the present disclosure can include one or more features that facilitate movement of the stented prosthesis through the tool. With this in mind, another tool 100 in accordance with principles of the present disclosure for compressing and/or loading a stented prosthesis (not shown) is provided in FIG. 6. The tool 100 can be akin in many respects to the tool 20 (FIG. 1) described above, and defines an entrance side 110 and an exit side 112 (the entrance and exit sides 110, 112 are referenced generally in FIG. 6). The tool 100 includes a housing 120 maintaining at least two sets of rollers, including a first set of rollers 122a and a second set of rollers 122b. The housing 120 can have any of the constructions described above. The first set of rollers 122a is located immediately adjacent the entrance side 110, whereas the second set of rollers 122b is located immediately adjacent the exit side 112. One or more additional sets of rollers can be provided intermediate the first and second sets of rollers 122a, 122b, such as third and fourth sets of rollers 122c, 122d as shown. The sets of rollers 122a-122d can have any of the constructions described above with the respect to the sets of rollers 42a-42e (FIG. 3A), each including two or more rollers (e.g., first and second rollers 130a, 132a identified in FIG. 6 for the first set of rollers 122a). Each of the rollers provided with the sets of rollers 120a-120d can have any of the constructions described in the present disclosure (e.g., the rollers 50a, 52a (FIG. 2A)). The sets of rollers 122a-122d each define a working region having a working diameter that progressively decreases from the entrance side 110 to the exit side 112 commensurate with the descriptions above.

In addition, the tool 100 includes one or more mechanisms configured to facilitate user-actuated rotation of the rollers of the sets of rollers 122a-122d. For example, a first gear assembly 140a (referenced generally) is associated with the first set of rollers 130a, and includes first and second gears 150, 152, and a handle 154. The first gear 150 is connected to the first roller 130a (e.g., via a pin or axle 156 (referenced generally)) and the second gear 152 is connected to the second roller 132a (e.g., via a pin or axle 158 (referenced generally)). With this construction, the first roller 130a rotates with rotation of the first gear 150 and the second roller 132a rotates with rotation of the second gear 152. Further, the first and second gears 150, 152 are configured and arranged to be in meshed engagement. Finally, the handle 154 is attached to the pin 156 and thus the first gear 150. The first gear assembly 140a is constructed such that a user-applied torque or rotational force at the handle 154 causes the first and second rollers 130a, 130b to rotated in tandem via the meshed gears 150, 152. Similarly-configured gear assemblies 140b-140d can be provided with the remaining sets of rollers 122b-122d, respectively. In some embodiments, a location the handle 154 of each successive gear assembly 140a-140d can alternate relative to the opposing sides of the housing 120 so as to accommodate a larger-sized handle. In other embodiments, two or more or all of the gear assemblies 140a-140d can be linked to one another (such that a lesser number of handles is required). In yet other embodiments, one or more or all of the gear assemblies 140a-140d can be driven by a motor or similar device. Regardless, the tool 100 can be operated to compress or collapse a stented prosthesis consistent with the descriptions above.

Figure 7A:
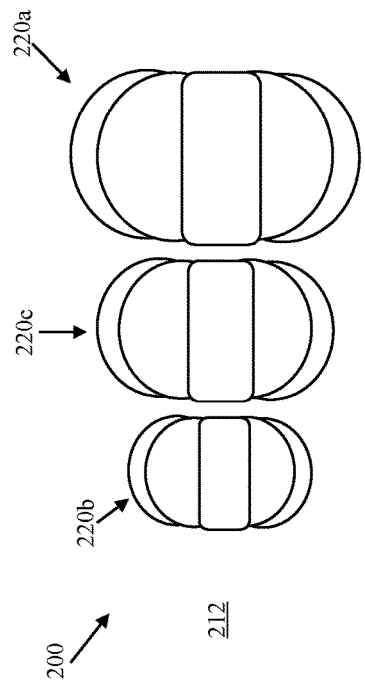
FIG. 7A schematically illustrates portions of another tool in accordance with principles of the present disclosure.

Portions of another embodiment tool 200 in accordance with principles of the present disclosure for compressing or collapsing a stented prosthesis (not shown) are illustrate in simplified form in FIG. 7A. The tool 200 defines an entrance side 210 (referenced generally) opposite an exit side 212 (referenced generally), and include two or more sets of rollers, such as a first set of rollers 220a and a second set of rollers 220b. The first set of rollers 220a is arranged immediately adjacent the entrance side 210, and the second set of rollers 220b is arranged immediately adjacent the exit side 212. One or more additional sets of rollers can be provided intermediate the first and second sets of rollers 220a, 220b, such as a third set of rollers 220c. Though not shown, the tool 200 further includes a housing that rotatably maintains the rollers of the sets of rollers 220a-220c as described below.

Figure 7B:
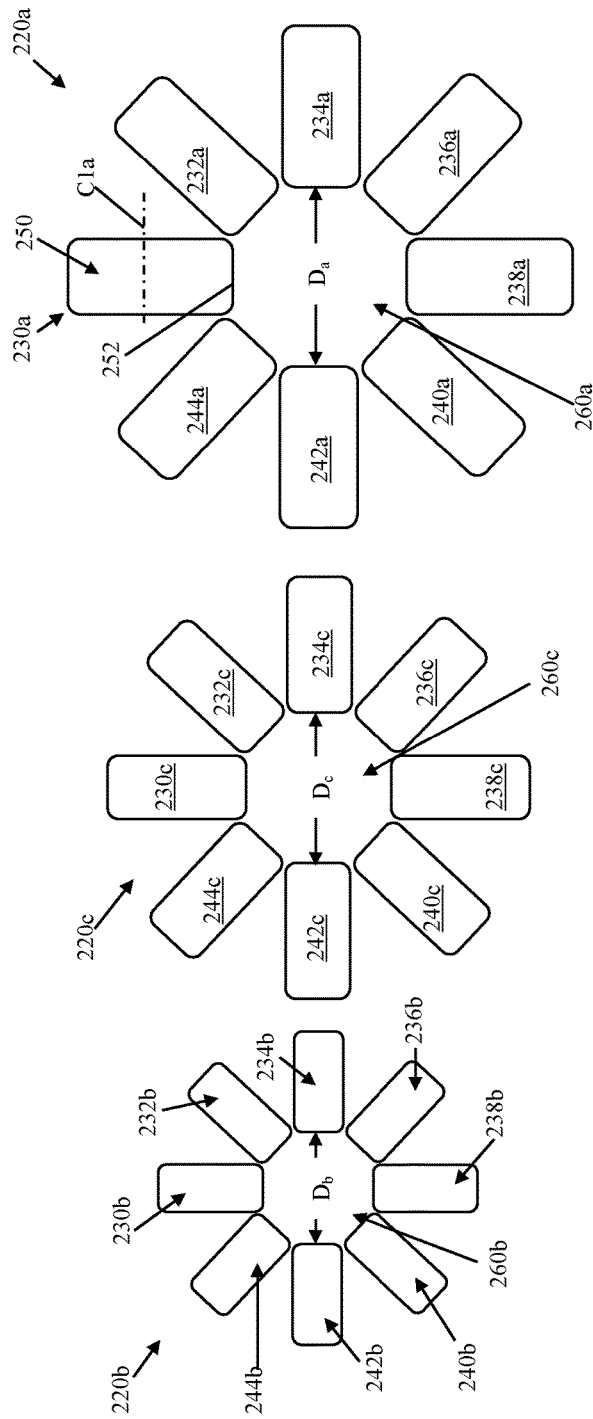
FIG. 7B is an exploded end view of sets of rollers provided with the tool of FIG. 7A.

The first-third sets of rollers 220a-220c are shown in isolation in FIG. 7B. With cross-reference between FIGS. 7A and 7B, the first set of rollers 220a includes a plurality of rollers, such as rollers 230a-244a. The rollers 230a-244a can be identical in size, shape and construction. Although eight of the rollers 230a-244a are shown, any other number, either greater or lesser, is also acceptable. Each of the rollers 230a-244a are maintained by the tool 200 so as to be rotatable about a central axis (central axis C1a identified for the first roller 230a in FIG. 7B). An engagement section 250 (identified for the first roller 230a) provides an outer surface 252 adapted to interface with a stented prosthesis as described above, with the rollers 230a-244a being arranged in a circular pattern so as to define a working region 260a. The working region 260a has a circle or circular-like shape, and defines a working diameter $D_a$. Depending upon a size and shape of each of the rollers 230a-244a as well as the number of rollers provided, the collectively-defined working region 260a may be more or less circular in shape than reflected by FIG. 7B, and the working diameter $D_a$ may or may not be uniform or consistent about an entirety of the working region 260a.

The second and third sets of rollers 220b, 220c can be akin to the first set of rollers 220a, including a plurality of rollers, such as rollers 230b-244b, 230c-244c, respectively. As reflected by the views, a size or diameter of the intermediate rollers 230c-244c can be less than that of the first (or entrance side) rollers 230a-244a, and greater than that of the rollers 230b-244b of the second (or exit side) set of rollers 220b. Regardless, the third set of rollers 220c defines a working region 260c having a working diameter $D_c$ that is less than the working diameter $D_a$ of the first set of rollers 220a; the second set of rollers 220b defines a working region 260b having a working diameter $D_b$ that is less than the working diameter $D_c$ of the third set of rollers 220c. The working diameters $D_a$-$D_c$ progressively decrease from the entrance side 210 to the exit side 212 as described above. During use, a stented prosthesis (not shown) is progressively compressed or crimped when successively interfacing or being forced through the first-third sets of rollers 220a-220c from the entrance side 210 to the exit side 212 as described above.

Figure 8A:
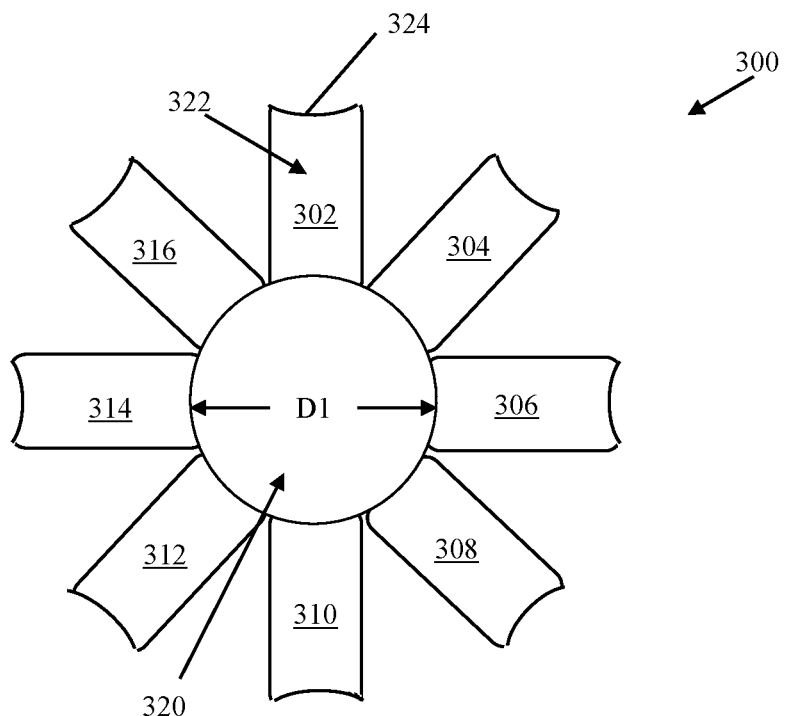
FIG. 8A is a simplified end view of another set of rollers useful with the tools of the present disclosure.
Figure 8B:
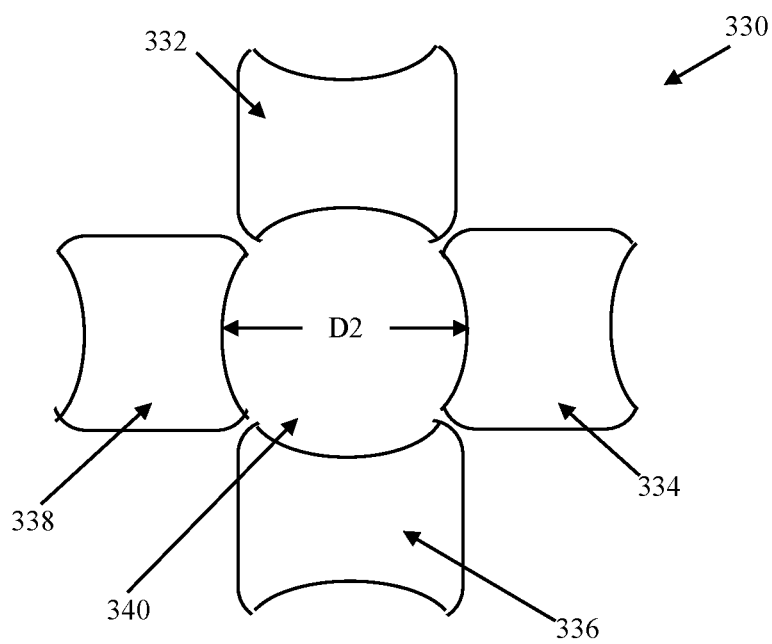
FIG. 8B is a simplified end view of another set of rollers useful with the tools of the present disclosure.

The tools of the present disclosure can incorporate other roller constructions, as well as other patterns or arrangements of rollers to generate any of the working regions described above. For example, FIG. 8A schematically illustrates a set of rollers 300 useful with any of the tools of the present disclosure, and including eight rollers 302-316. The rollers 302-316 can be identical and are arranged to collectively define a working region 320 having a working diameter D1. As compared to the rollers 230a-244a (FIG. 7B) of the tool 200 (FIG. 7A), the rollers 302-316 each include an engagement section 322 having an outer surface 324 defining a concave shape. Another embodiment set of rollers 330 useful with any of the tools of the present disclosure is shown in FIG. 8B, and includes four rollers 332-338. The rollers 332-338 can be identical and are arranged to collectively define a working region 340 having a working diameter D2.

The tools of the present disclosure can be useful in collapsing or compressing a variety of differently-formatted stented prostheses. In some embodiments, the tools and methods of the present disclosure relate to stented transcatheter prosthetic heart valves, such as a bioprosthetic heart valve having tissue leaflets or a synthetic heart valve having polymeric, metallic or tissue-engineered leaflets, and can be specifically configured for replacing any of the four valves of the human heart. The stented prosthetic heart valve useful with the tools and methods of the present disclosure can be generally used for replacement of a native aortic, mitral, pulmonic or tricuspid valve, or to replace a failed bioprosthesis, such as in the area of an aortic valve or mitral valve, for example.

In general terms, the stented prosthetic heart valves useful with the tools and methods of some embodiments of the present disclosure include a stent or stent frame maintaining a valve structure (tissue or synthetic), with the stent frame having a normal, expanded condition or arrangement and collapsible to a compressed condition or arrangement for loading within a delivery device. The stent frame is normally constructed to self-deploy or self-expand when release from the delivery device. In other embodiments, stent frames useful with systems and devices of the present disclosure have a balloon-expandable configuration as is known in the art. The stents or stent frames are support structures that comprise a number of struts or wire segments arranged relative to each other to provide a desired compressibility and strength to the prosthetic heart valve. The struts or wire segments are arranged such that they are capable of transitioning from a compressed or collapsed condition to a normal, radially expanded condition. The struts or wire segments can be formed from a shape memory material, such as a nickel titanium alloy (e.g., Nitinol™). The stent frame can be laser-cut from a single piece of material, or can be assembled from a number of discrete components.

Figure 9A:
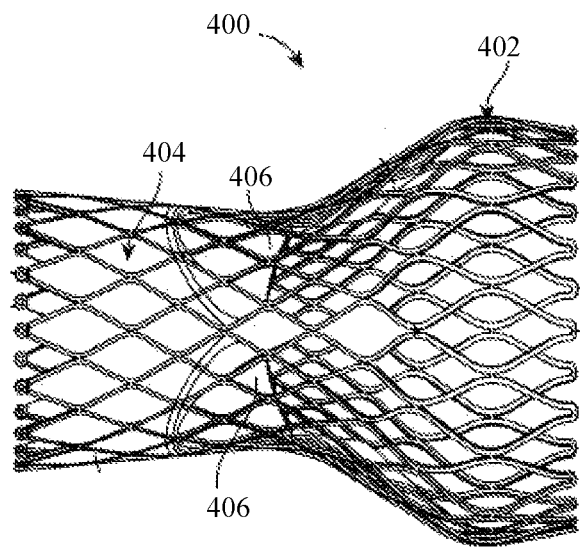
FIG. 9A is a side view of a stented prosthetic heart valve in a normal state and that can be compressed by tools of the present disclosure.
Figure 9B:
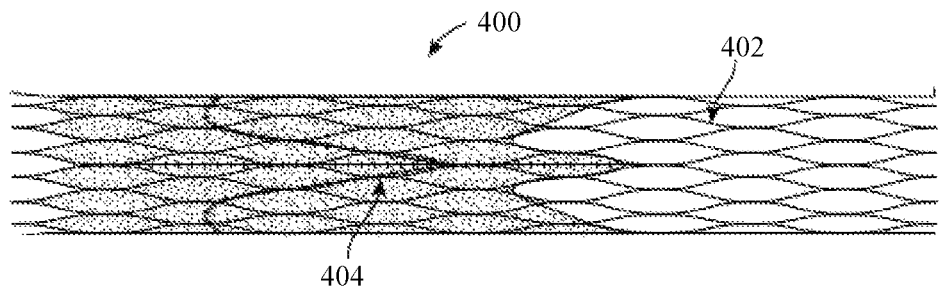
FIG. 9B is a side view of the stented prosthetic heart valve of FIG. 9A in a compressed state.

With the above understanding in mind, one simplified, non-limiting example of a stented prosthetic heart valve 400 useful with tools and methods of the present disclosure is illustrated in FIG. 9A. As a point of reference, the stented prosthetic heart valve 400 is shown in a normal or expanded condition in the view of FIG. 9A; FIG. 9B illustrates the stented prosthetic heart valve 400 in a compressed condition (e.g., when compressively retained within an outer catheter or sheath as described below). The stented prosthetic heart valve 400 includes a stent or stent frame 402 and a valve structure 404. The stent frame 402 can assume any of the forms mentioned above, and is generally constructed so as to be self-expandable from the compressed condition (FIG. 9B) to the normal, expanded condition (FIG. 9A). In other embodiments, the stent frame 402 can have a balloon-expandable configuration.

The valve structure 404 can assume a variety of forms, and can be formed, for example, from one or more biocompatible synthetic materials, synthetic polymers, autograft tissue, homograft tissue, xenograft tissue, or one or more other suitable materials. In some embodiments, the valve structure 404 can be formed, for example, from bovine, porcine, equine, ovine and/or other suitable animal tissues. In some embodiments, the valve structure 404 can be formed, for example, from heart valve tissue, pericardium, and/or other suitable tissue. In some embodiments, the valve structure 404 can include or form one or more leaflets 406. For example, the valve structure 404 can be in the form of a tri-leaflet bovine pericardium valve, a bi-leaflet valve, or another suitable valve. In some constructions, the valve structure 404 can comprise two or three leaflets that are fastened together at enlarged lateral end regions to form commissural joints, with the unattached edges forming coaptation edges of the valve structure 404. The leaflets 406 can be fastened to a skirt that in turn is attached to the frame 402.

Figure 10:
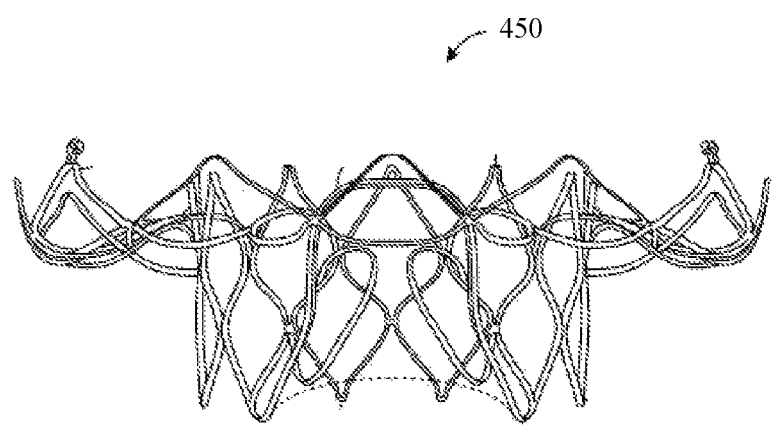
FIG. 10 is a side view of a stent of another stented prosthetic heart valve that can be compressed by tools of the present disclosure.

With the one exemplary construction of FIGS. 9A and 9B, the stented prosthetic heart valve 400 can be configured (e.g., sized and shaped) for replacing or repairing an aortic valve. Alternatively, other shapes are also envisioned, adapted to mimic the specific anatomy of the valve to be repaired (e.g., stented prosthetic heart valves useful with the present disclosure can alternatively be shaped and/or sized for replacing a native mitral, pulmonic or tricuspid valve). For example, FIG. 10 illustrates another non-limiting example of a stent frame 450 portion of another stented prosthetic heart valve with which the tools and methods of the present disclosure are useful. In the normal or expanded condition of FIG. 10, the stent frame 450 can be sized and shaped for mitral valve implantation. The stent frame 450 can be forced and constrained to a compressed condition (not shown, but akin to the shape of FIG. 9A) during delivery, and will self-expand to the natural condition of FIG. 10 upon removal of the constraining force(s).

Alternatively, the tools and methods of the present disclosure can be used to compress or crimp other stented prosthesis formats that may or may not include a prosthetic valve.

EXAMPLES

Objects and advantages of the present disclosure are further illustrated by the following non-limiting examples and comparative examples. The particular materials and amounts thereof recited in these examples, as well as other conditions and details, should not be construed to unduly limit the present disclosure.

An example compressing tool in accordance with the tool 20 of FIG. 1 was prepared. The tool included five sets of rollers, with each set of rollers having two rollers. The set of rollers at an entrance side of the tool established a working region having a working diameter of 0.275 inch (6.985 mm); the immediately-next set of rollers established a working region having a working diameter of 0.265 inch (6.731 mm); the next set of rollers established a working region having a working diameter of 0.255 inch (6.477 mm); the next set of rollers established a working region having a working diameter of 0.250 inch (6.350 mm); and the final or exit side set of rollers established a working region having a working diameter of 0.245 inch (6.223 mm).

Use of the example compressing tool was evaluated with a stented prosthetic heart valve available under the trade designation CoreValve® from Medtronic, Inc. The stented prosthetic heart valve was processed through the example compressing tool and immediately loaded into the capsule of a CoreValve® delivery system available from Medtronic, Inc. Following collapsing and loading, a diameter of the capsule was measure and found to be approximately 0.270 inch (21-21 Fr). The capsule was visually inspected, and no bulges or bumps were found. For comparison, similar CoreValve® stented prosthetic heart valves were collapsed and loaded into the capsule of a CoreValve® delivery system using a funnel-based tool commonly employed for compressing and loading a stented prosthetic heart valve and using an iris-type stent crimping tool available from Machine Solutions, Inc. Following compressing and loading, the resultant capsules were measure and visually inspected. Capsules loaded with the CoreValve® prosthetic heart valve using either the funnel-based tool or the iris-type crimping tool had a diameter in the range of 0.295-0.325 inch (23-25 Fr) and exhibited bulges or bumps. Thus, the example compressing tool was able to provide a reduced capsule diameter as compared to conventional tools (a reduction by as much as 4 Fr), with improved profile consistency.

Although the present disclosure has been described with reference to preferred embodiments, workers skilled in the art will recognize that changes can be made in form and detail without departing from the spirit and scope of the present disclosure.

What is claimed is:

1. A method of compressing a stented prosthesis, the method comprising:
 receiving a stented prosthesis in a first state defining a maximum outer diameter;
 inserting the stented prosthesis in the first state into a tool, the tool comprising:
  a first set of rollers at an entrance end of the tool and including a plurality of rollers arranged to collectively define a first working region having a first working diameter,
  a second set of rollers at an exit end of the tool and including a plurality of rollers arranged to collectively define a second working region having a second working diameter,
  wherein the first set of rollers is arranged relative to the second set of rollers such that the first and second working regions are axially aligned along a common centerline,
  and further wherein the first working diameter is greater than the second working diameter; and
 directing the stented prosthesis successively through the first set of rollers followed by the second set of rollers to compress the stented prosthesis to a second state having a maximum outer diameter less than the maximum outer diameter of the first state, wherein the step of directing includes:

the plurality of rollers of the first set of rollers in contact with at least a majority of a circumference of the stented prosthesis in a plane perpendicular to the common centerline as the stented prosthesis passes through the first set of rollers, and the plurality of rollers of the second set of rollers in contact with at least a majority of the circumference of the stented prosthesis in a plane perpendicular to the common centerline as the stented prosthesis passes through the second set of rollers.

2. The method of claim 1, wherein the step of directing includes exerting an increasing compressive force on to the stented prosthesis as the stented prosthesis is progressively directed through the tool.

3. The method of claim 1, wherein after the step of directing, the method further comprising:

manipulating the tool to release the stented prosthesis.

4. The method of claim 1, wherein the stented prosthesis is a stented prosthetic heart valve.

5. The method of claim 1, wherein after the step of directing, the method further comprising:

loading the stented prosthesis in the second state onto a delivery system.

6. The method of claim 5, wherein the stented prosthesis is a stented prosthetic heart valve, the delivery system is a transcatheter delivery system, and the step of loading includes the transcatheter delivery system maintaining the stented prosthetic heart valve in the second state.

7. The method of claim 1, wherein the step of directing includes rotating a handle connected by gears to the plurality of rollers of the first set of rollers, causing the plurality of rollers of the first set of rollers to rotate.

8. The method of claim 1, wherein each of the plurality of rollers of the first set of rollers and of the second set of rollers defines a central axis about which the respective roller rotates, and further wherein the central axes are all substantially parallel with one another.

* * * * *